United States Patent  (10) Patent No.: US 7,254,446 B1
Erickson et al.                                                                                      (45) Date of Patent:       Aug. 7, 2007

(54) SYSTEM AND METHOD FOR STIMULUS CALIBRATION FOR AN IMPLANTABLE PULSE GENERATOR

(75) Inventors: John H. Erickson, Plano, TX (US); Thomas K. Hickman, Plano, TX (US); Erik D. Engstrom, Murphy, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 179 days.

(21) Appl. No.: 11/073,026

(22) Filed: Mar. 4, 2005

Related U.S. Application Data

(60) Provisional application No. 60/550,040, filed on Mar. 4, 2004.

(51) Int. Cl.
*A61N 1/00* (2006.01)
*A61B 5/05* (2006.01)

(52) U.S. Cl. .............................. 607/46; 607/7; 607/11; 607/62; 607/63; 600/554

(58) Field of Classification Search ................. 607/2, 607/7, 11, 27, 28, 45, 46, 62; 600/554
See application file for complete search history.

(56) References Cited

U.S. PATENT DOCUMENTS 6,393,325 B1 * 5/2002 Mann et al. .................. 607/46
2004/0116978 A1 * 6/2004 Bradley ........................ 607/48

\* cited by examiner

*Primary Examiner*—Carl Layno
*Assistant Examiner*—Natasha Patel
(74) *Attorney, Agent, or Firm*—Peter R. Lando; Christopher S. L. Crawford

(57) ABSTRACT

A system, method, and computer program product for calibrating a stimulation device such as an implantable pulse generator (IPG). An IPG, whether it is a self-contained implantable pulse generator (SCIPG) or externally-powered implantable pulse generator (EPIPG), communicates with an external programmer to determine the characteristics of the stimuli delivered to the lead electrodes. An external programmer is used with patient feedback to determine initial threshold levels, and using the initial threshold levels, to determine threshold levels for combined electrode arrays.

21 Claims, 2 Drawing Sheets

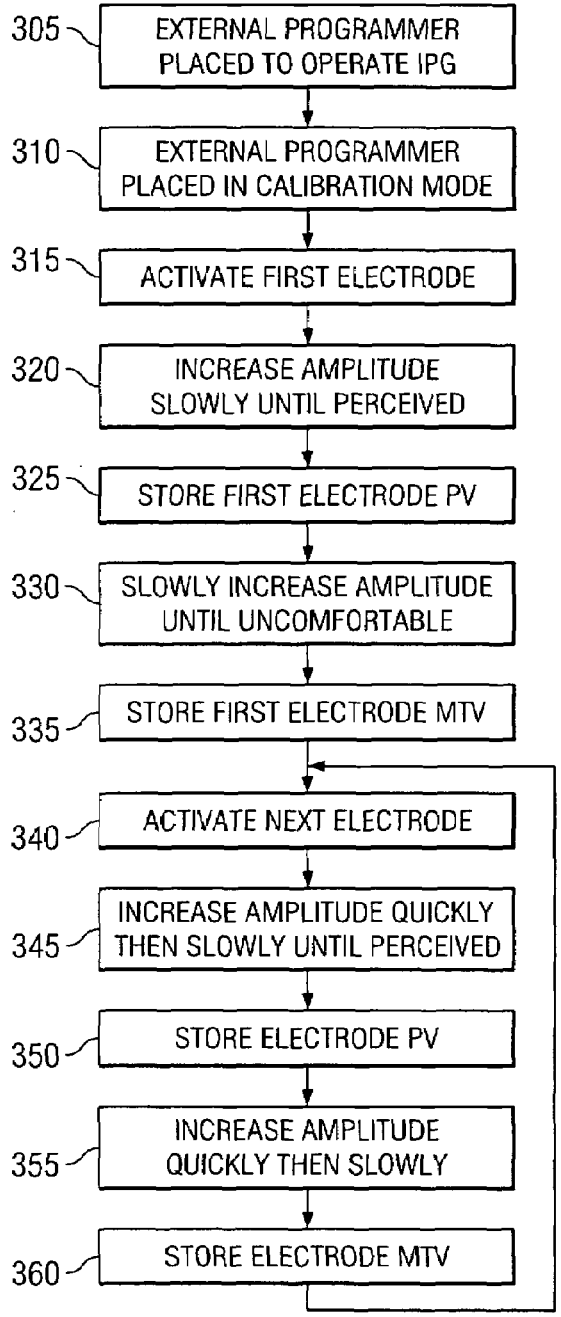
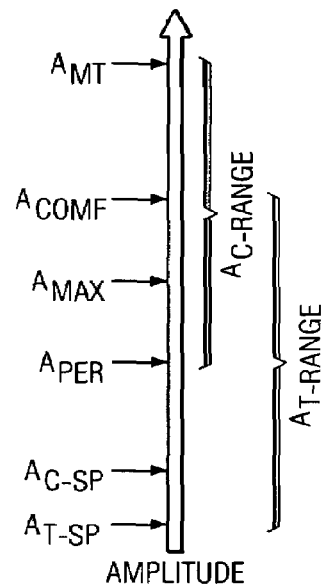
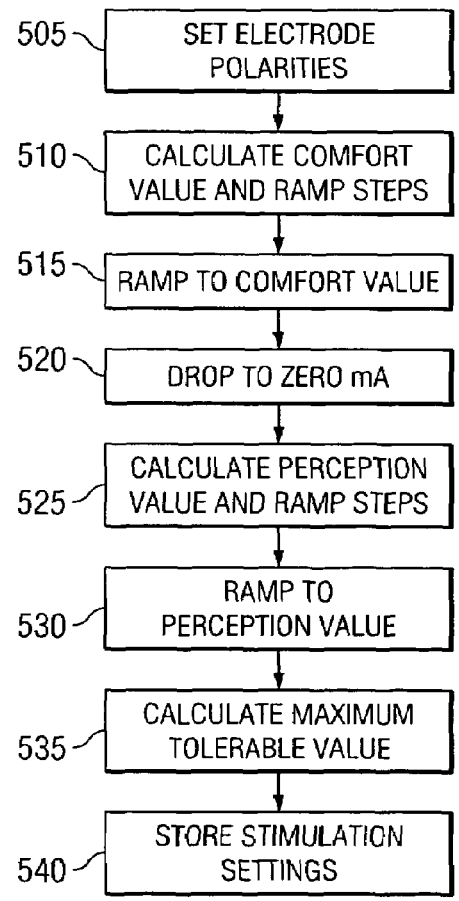

SYSTEM AND METHOD FOR STIMULUS CALIBRATION FOR AN IMPLANTABLE PULSE GENERATOR

CROSS-REFERENCE TO RELATED APPLICATIONS

This application claims priority benefit of U.S. Provisional Patent Application No. 60/550,040 entitled "SYSTEM AND METHOD FOR STIMULUS CALIBRATION FOR AN IMPLANTABLE PULSE GENERATOR," filed Mar. 4, 2004, the disclosure of which is hereby incorporated herein by reference. This application is related to concurrently filed "SYSTEM AND METHOD FOR GENERATING AND TESTING TREATMENT PROTOCOLS", application Ser. No. 11/072,998, the disclosure of which is hereby incorporated herein by reference.

TECHNICAL FIELD OF THE INVENTION

The present invention is directed, in general, to medical devices and more specifically to neurostimulation devices.

BACKGROUND OF THE INVENTION

The present invention relates to stimulation systems, for example, spinal cord, peripheral, and deep-brain stimulation systems. A spinal cord stimulation system is an implantable pulse generating system used to provide electrical stimulation pulses from an electrode array placed epidurally or surgically near a patient's spine. An implanted pulse generator (IPG) may operate independently to provide the required electrical stimulation, or may interact with an external programmer, which delivers programming and/or control information and/or energy for the electrical stimulation, typically through a radio-frequency (RF) or other wireless signal.

Spinal cord stimulation (SCS) is a well accepted clinical method for reducing pain in certain populations of patients. SCS systems typically include an implanted device, lead wires, and electrodes connected to the lead wires. The implanted device receives signals from an external programmer, and transmits corresponding electrical pulses that are delivered to the spinal cord (or other tissue) through the electrodes which are implanted along the dura of the spinal cord. In a typical situation, the attached lead wires exit the epidural space and are tunneled around the torso of the patient to a subcutaneous pocket where the device is implanted.

Spinal cord and other stimulation systems are known in the art. For example, in U.S. Pat. No. 3,646,940, there is disclosed an implantable electronic stimulator that provides timed sequenced electrical impulses to a plurality of electrodes so that only one electrode has a voltage applied to it at any given time. Thus, the electrical stimuli provided by the apparatus taught in the '940 patent comprise sequential, or non-overlapping, stimuli.

In U.S. Pat. No. 3,724,467, an electrode implant is disclosed for the neurostimulation of the spinal cord. A relatively thin and flexible strip of physiologically inert plastic is provided with a plurality of electrodes formed thereon. The electrodes are connected by leads to an RF receiver, which is also implanted, and which is controlled by an external controller. The implanted RF receiver has no power storage means for generating electrical stimulations, and must be coupled to the external controller in order for neurostimulation to occur.

In U.S. Pat. No. 3,822,708, another type of electrical spinal cord stimulating device is shown. The device has five aligned electrodes which are positioned longitudinally on the spinal cord and transversely to the nerves entering the spinal cord. Current pulses applied to the electrodes are said to block sensed intractable pain, while allowing passage of other sensations. The stimulation pulses applied to the electrodes are approximately 250 microseconds in width with a repetition rate of 5 to 200 pulses per second. A patient-operable switch allows the patient to change which electrodes are activated, i.e., which electrodes receive the current stimulus, so that the area between the activated electrodes on the spinal cord can be adjusted, as required, to better block the pain.

Other representative patents that show spinal cord stimulation systems or electrodes include U.S. Pat. Nos. 4,338,945; 4,379,462; 5,121,754; 5,417,719, 5,501,703, and 6,516,227. All of the patents noted above are hereby incorporated by reference.

A typical IPG is self contained, having a multi-year battery pack and a single treatment program, and is generally programmed during or immediately following implantation in the patient's body.

Other SCS systems have no implanted power source, but receive power and programming and/or control information from an external transmitter. These systems will convert the RF signals from the transmitter to provide power to the implanted receiver, and use the RF programming information to determine the intensity, location, and duration of the electrical pulses delivered to the electrodes.

In either case, before the IPG can be properly programmed, stimulation thresholds must be determined so that the pulse stimuli the IPG delivers is strong enough to effectively treat the patient, but not so strong that the treatment is uncomfortable or painful for the patient.

Unfortunately, this process is generally inconvenient and time consuming for both the patient and the professional performing the threshold determination. For example, typical systems start each electrode amplitude at zero and ramp linearly until a maximum tolerance is determined. In some known cases, this process is shortened by only determining a small number of the lead electrode parameters, and estimating or guessing proper parameters for the remaining electrodes. This method can lead to ineffective or uncomfortable treatments.

There is, therefore, a need in the art for a system, process and device for improved IPG calibration techniques.

SUMMARY OF THE INVENTION

In one embodiment of the present invention, there is a system, method, and computer program product for calibrating a stimulation device such as an implantable pulse generator (IPG). The IPG, whether it is a self-contained implantable pulse generator (SCIPG) or externally-powered implantable pulse generator (EPIPG), communicates with an external programmer to determine the characteristics of the stimuli delivered to the lead electrodes. An external programmer is used, with patient feedback, to determine initial threshold levels, and using the initial threshold levels, to determine threshold levels for combined electrode arrays.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art will appreciate that they may readily use the conception and the specific embodiment disclosed as a basis for modifying or designing other structures for carrying out the same purposes of the present invention. Those skilled in the art will also realize that such equivalent constructions do not depart from the spirit and scope of the invention in its broadest form.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which:

FIG. 3 depicts a flowchart of a process in accordance with an embodiment of the present invention;

FIG. 4 depicts a diagram of relative amplitude measurements for electrode calibration; and FIG. 5 depicts a flowchart of a process in accordance with an embodiment of the present invention.

DETAILED DESCRIPTION OF THE INVENTION

FIGS. 1 through 5, discussed below, and the various embodiments used to describe the principles of the present invention in this patent document are by way of illustration only and should not be construed in any way to limit the scope of the invention. Those skilled in the art will understand that the principles of the present invention may be implemented in any suitably arranged device. The numerous innovative teachings of the present application will be described with particular reference to the presently preferred embodiment.

In embodiments of the present invention, there are an apparatus and methods for calibrating and/or testing a stimulation device such as, for example, an implantable pulse generator (IPG). The PG, whether it is a self-contained implantable pulse generator (SCIPG) or externally-powered implantable pulse generator (EPIPG), communicates with an external programmer to determine the characteristics of the stimuli delivered to the lead electrodes. An external programmer is used, with patient feedback, to determine initial threshold levels, and using the initial threshold levels, to determine threshold levels for combined electrode arrays.

The techniques disclosed herein can be used in any implantable medical device, such as a pump, deep-brain stimulation system, etc.

As used herein, an SCIPG is an IPG having an implanted power source, such as a long-lasting or rechargeable battery. An EPIPG is an IPG which receives at least some of its operating power from an external power transmitter, preferably in the form of a RF signal. The external power transmitter, in the preferred embodiment, is built into the external programmer.

Figure 1:
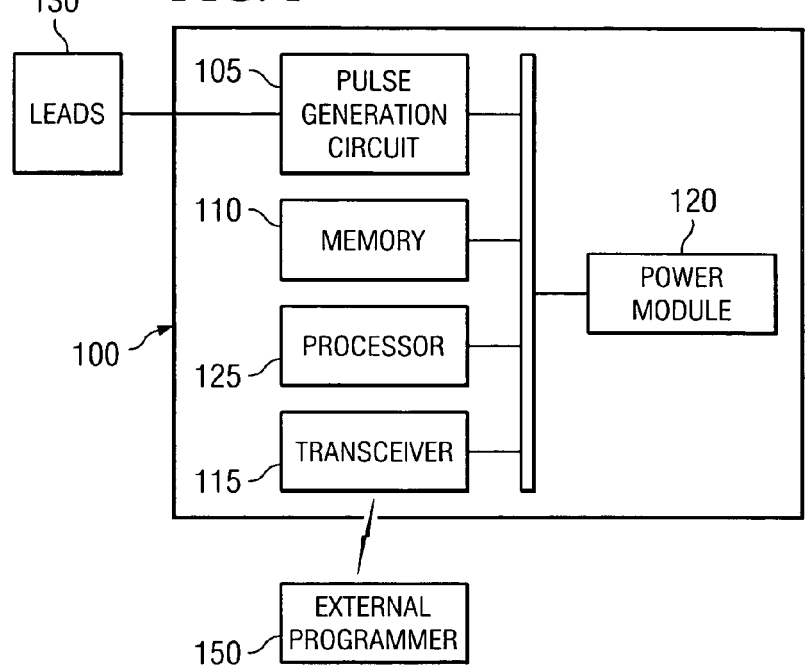
FIG. 1 depicts a block diagram of an implantable pulse generator in accordance with a preferred embodiment of the present invention.

FIG. 1 shows a diagram of the components of an IPG 100 in accordance with the preferred embodiment. The implanted device comprises, but is not limited to, a pulse generation circuit 105, a non-volatile memory 110, a transceiver 115, a power module 120, and a processor 125. Memory 110 may also include volatile memory (not shown).

In an SCIPG, the power module 120 will include a long-term battery or a rechargeable battery and a voltage detection, and regulation circuit. In an EPIPG, and in an SCIPG with a rechargeable battery, the power module 120 will include a circuit for converting radio-frequency (RF) energy (or other energy) into direct current. In either case, the power module 120 is connected to power the processor 125 and the pulse generation circuit 105.

One example of an SCIPG may be an SCIPG manufactured by Advanced Neuromodulation Systems, Inc. such as the Genesis® system, part number 3608. One example of the EPIPG may be an EPIPG manufactured by Advanced Neuromodulation Systems, Inc. such as the Renew® system, part number 3416.

The pulse generation circuit 105 is connected to receive power from power module 120 and to be controlled by processor 125. Processor 125 is connected to receive power from power module 120 and to read from, and write to, non-volatile memory 110. Further, processor 125 is connected to receive and decode data from transceiver 115. Note that in different embodiments, transceiver 115 may only be a receiver, while in preferred embodiments, processor 125 is connected to also transmit data via transceiver 115. Further, in various embodiments, transceiver 115 receives power signals for operating or recharging the IPG, transmits, and receives.

Transceiver 115 is positioned to receive RF commands from an external programmer 150, and to deliver these commands to processor 125. Further, in an EPIPG, the receiver 115 is configured to receive RF power signals, and to deliver these to power module 120.

Non-volatile memory 110 contains programming and control data, and can be written to and read from by processor 125.

Leads 130 are implanted in the patient's epidural space (or other locations), as described above or known to those of skill in the art. Leads 130 connect with pulse generation circuit 105, optionally via lead extensions (not shown).

Leads 130, in one embodiment, have multiple electrodes, each of which can be independently controlled by the pulse generation circuit 105. Each electrode can be individually set as a positive (acting as an anode), a negative (acting as a cathode), or to a high impedance (turned off). The pulse generation circuit 105, under control of the processor 125, also controls the pulse amplitude, pulse width, and pulse frequency to each electrode on the leads 130.

Also shown here, although not a part of the IPG 100 itself, is external programmer 150, which communicates with transceiver 115. External programmer 150 can be either an external patient programmer (EPP), which is typically carried and operated by the patient, or an advanced programmer, which is typically operated by the patient's physician or clinician. External programmer 150 will typically communicate with transceiver 115 via an antenna (not shown), placed on or near the patient's body proximal to the IPG 100, via near-field or far-field technology.

Figure 2:
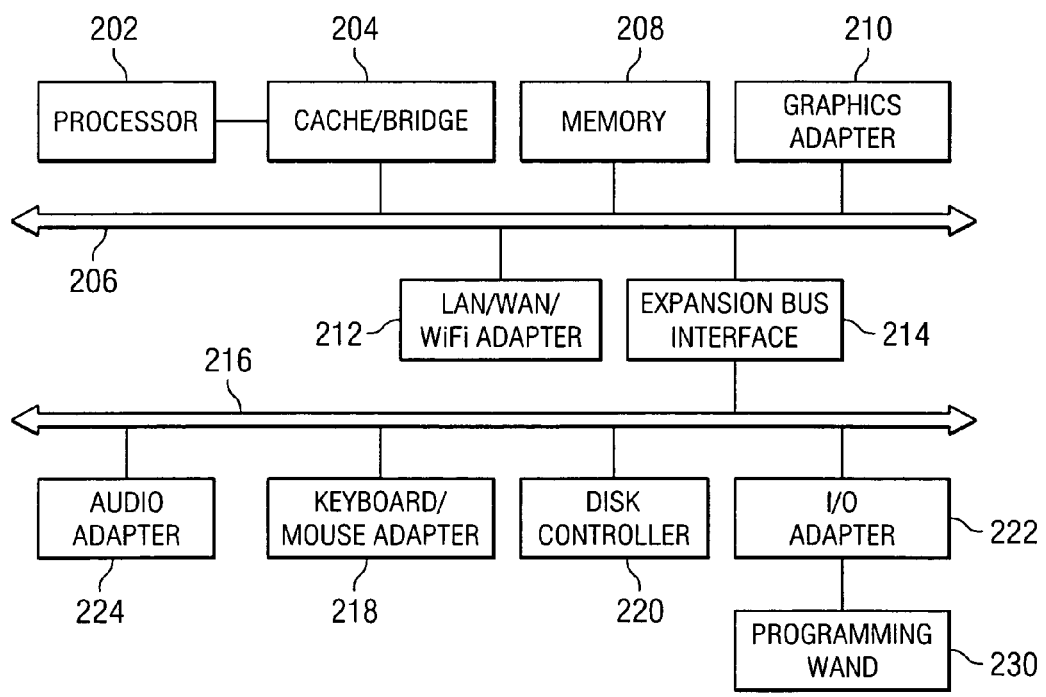
FIG. 2 depicts a block diagram of a data processing system in which various embodiments of the present invention can be implemented.

FIG. 2 depicts a data processing system in which a preferred embodiment of the present invention may be implemented, as any of the disclosed data processing systems, and in particular as a data processing system serving as an external programmer. The data processing system depicted includes a processor 202 connected to a level two cache/bridge 204, which is connected in turn to a local system bus 206. Local system bus 206 may be, for example, a peripheral component interconnect (PCI) architecture bus.

Also connected to local system bus in the depicted example are a main memory 208 and a graphics adapter 210.

Other peripherals, such as local area network (LAN)/Wide Area Network (WAN)/Wireless (e.g. WiFi) adapter 212, may also be connected to local system bus 206. Expansion bus interface 214 connects local system bus 206 to input/output (I/O) bus 216. I/O bus 216 is connected to keyboard/mouse adapter 218, disk controller 220, and I/O adapter 222.

Also connected to I/O bus 216 in the example shown is audio adapter 224, to which speakers (not shown) may be connected for playing sounds. Keyboard/mouse adapter 218 provides a connection for a pointing device (not shown), such as a mouse, trackball, trackpointer, etc.

Connected to the I/O adapter 222 is programming wand 230. Programming wand 230 is used to communicate with an IPG as shown in FIG. 1, in the manner and for the functions described herein. In other embodiments, the I/O adapter 222 is connected, to communicate with an IPG through an external programmer or advanced programmer.

Those of ordinary skill in the art will appreciate that the hardware depicted in FIG. 2 may vary in particular. For example, other peripheral devices, such as an optical disk drive and the like, also may be used in addition or in place of the hardware depicted. The depicted example is provided for the purpose of explanation only and is not meant to imply architectural limitations with respect to the present invention.

A data processing system in accordance with a preferred embodiment of the present invention includes an operating system employing a graphical user interface. The operating system permits multiple display windows to be presented in the graphical user interface simultaneously, with each display window providing an interface to a different application or to a different instance of the same application. A cursor in the graphical user interface may be manipulated by a user through the pointing device. The position of the cursor may be changed and/or an event, such as clicking a mouse button, generated to actuate a desired response.

One of various commercial operating systems, such as a version of Microsoft Windows™ a product of Microsoft Corporation located in Redmond, Wash. may be employed if suitably modified. The operating system is modified or created in accordance with the present invention as described.

In a conventional EPIPG, the external programmer is used to send both a power signal and pulse-generation instructions, on a real-time basis, to the EPIPG. In this case, the programming for the EPIPG is stored on the external programmer.

A program consists of one or more stimulation settings, also referred to herein as "stimsets." The programmed stimulation settings specifically define and characterize the administered electric pulse stimulation. Other information related to stimulation settings, applications, and pain management, not necessary for an understanding of the presently preferred embodiments, is found in U.S. Pat. No. 5,938,690, filed 7 Jun. 1996 and issued 17 Aug. 1999, U.S. Pat. No. 6,609,031, filed 7 Jun. 1996 and issued 19 Aug. 2003, and U.S. patent application Ser. No. 10/120,953, filed 11 Apr. 2002 and published 22 Aug. 2002 as United States Patent Application Publication No. 2002/0116036, all of which are hereby incorporated by reference.

In one embodiment, each stimset is comprised of an electrode configuration and stimulation amplitude, stimulation frequency, and/or stimulation pulse width, and those of skill in the art will recognize that other parameters can be included. The electrode configuration defines whether each electrode is on or off and, if on, the polarity of that electrode. The amplitude is the intensity of the applied electric pulse. The frequency is the number of times the electrodes are turned on each second. The pulse width is the amount of time the pulse is left on during each cycle.

A program is defined as having at least one stimset, and generally corresponds to providing a treatment relating to a specific part of a patient's body. A program can have multiple stimsets; in this case, each stimset is applied sequentially, repeatedly, and/or randomly. Preferably, each program is applied so that the patient experiences the combined effect of each stimset, as if they were being applied simultaneously.

For example, a first stimset may provide relief to a patient's right leg, and a second stimset may provide relief to a patient's left leg. According to one embodiment, then, there will be at least three programs stored in the patient's programmer:

Program 1 comprises the first stimset;
Program 2 comprises the second stimset; and
Program 3 comprises both the first and second stimsets.

In this case, when the patient uses program 1 on the IPG, she would feel relief in her right leg, program 2 would provide relief in her left leg, and program 3 would provide relief in both legs.

A program comprising more than one stimset is referred to herein as a "multistim program."

In one embodiment, the programmer is capable of storing up to 24 different programs, each program having up to 8 stimsets. Of course, in other embodiments, the programmer can store a much greater number of programs, each having associated a much greater number of stimsets. In certain embodiments, the IPG itself can store various numbers of programs having varying numbers of stimsets.

In the preferred embodiment, all active electrodes in a stimset receive the same stimulation input, including the same pulse width, pulse frequency, and pulse amplitude. Each electrode in the stimset is assigned a polarity of positive, negative, or off. For example, a first stimset for an 8-electrode lead can be defined as having an amplitude of approximately 4 mA, delivered with a 280 microsecond pulse width and an 80 Hz frequency, with the following electrode polarities, with "+" indicating a positive polarity (anode), "−" indicating a negative polarity (cathode), and "0" indicates that the electrode is off:

| Electrode # | 0 | 1 | 2 | 3 | 4 | 5 | 6 | 7 |
|---|---|---|---|---|---|---|---|---|
| Polarity | + | + | 0 | 0 | − | − | + | 0 |

Note that in the preferred embodiment, every stimset must have at least one anode and one cathode. In an alternate embodiment, the IPG itself can act as an anode. A second stimset for an 8-electrode lead can be defined as having an amplitude of approximately at 4.2 mA, delivered with a 240 microsecond pulse width and an 80 Hz frequency, with the following electrode polarities:

| Electrode # | 0 | 1 | 2 | 3 | 4 | 5 | 6 | 7 |
|---|---|---|---|---|---|---|---|---|
| Polarity | − | − | 0 | + | − | 0 | + | 0 |

Then, if a multistim program contains both the first and second stimset (as in the exemplary Program 3, above), as in the program is executed, the IPG will rapidly alternate between the first and second stimsets, so that the patient experiences the combined effect of both stimsets in the multistim program. In the currently preferred embodiment, all stimsets in a program have the same frequency, but other embodiments allow for different frequencies in a single program.

A typical pulse, in a preferred embodiment, is approximately 4V-5V at 4 mA, delivered with a 280 microsecond pulse width and an 80 Hz frequency. Those of skill in the art will recognize that the pulse amplitude can also be defined in volts.

Before the IPG can be programmed, however, the IPG must be calibrated to ensure that a proper stimulus is generated for each lead electrode.

FIG. 3 depicts a flowchart of a process for calibrating the IPG for the individual patient. Note that this process is used to program an already-implanted IPG; a similar process can be used to program the IPG during implantation.

This process is typically performed by a physician or other professional using an external programmer as described herein. Generally, this programming process is not one that would normally be performed by a patient, but could be so if the patient were properly trained.

First, a programming wand will be placed in a location proximate to the IPG or the IPG antenna (step 305). In other embodiments, "far-field" programming can be used. Next, preferably using an RF signal, the external programmer will be placed into calibration mode (step 310).

The external programmer is then used to instruct the IPG to activate one electrode combination on the PG lead with a minimal pulse amplitude (step 315). The external programmer is then used to slowly increase the pulse amplitude to that electrode combination until the patient indicates that she can sense the delivered stimulation (step 320). The external programmer will store the current amplitude as the perception value (PV) for that electrode (step 325).

Typically, the electrodes are activated in pairs for this process, with the electrode to be targeted set as a cathode. For example, to calibrate the first electrode, the electrode pair 1 and 2 could be used, with, electrode 1 set as a cathode and electrode 2 set as an anode, the rest of the electrodes set as off.

The external programmer is then used to slowly increase the pulse amp to the electrode combination in a predetermined fashion, preferably in a linear fashion, until the patient indicates that the delivered stimulation is uncomfortable (step 330). The external programmer will store the current amplitude as the maximum tolerable value (MTV) for that electrode (step 335). The first electrode combination, is now calibrated for PV and MTV.

Because a patient's perception of the stimulus in proximate electrodes is relatively constant, the PV for the electrode is used as a predictor value for more quickly calibrating the subsequent electrodes. In the preferred embodiment, the MTV is only calibrated for the first electrode combination.

The external programmer is then used to instruct the IPG to activate the next electrode on the IPG lead with a minimal pulse amplitude (step 340). The external programmer is then used to more quickly increase the pulse amplitude to the electrode until the amplitude nears the PV of the previous electrode combination, then slowly increase until the patient senses the stimulation (step 345). The external programmer will store the current amplitude as the perception value (PV) for that electrode (step 350).

In this embodiment, the amplitude is increased in increments equal to approximately ⅓ of the remaining differential between the current amplitude and the PV of the first electrode. In this way, while the amplitude ramp-up of the first electrode was according to a first predetermined function, preferably substantially linear, the ramp-up of the remaining electrodes is according to a second predetermined function, preferably in a non-linear manner or closer to a logarithmic rate. This approach provides an efficient means of quickly bringing the electrode amplitude to near the target value (the previous electrode PV), but slowly increasing as the amplitude nears or passes the first electrode PV, so as to accurately calibrate the PV for that electrode. If additional MTVs are not to be determined, as in the preferred embodiment, the process repeats at step 340 until all PVs are determined.

In a similar manner, if the MTV for each electrode is to be determined, as according to an alternate embodiment, the external programmer is then used to more quickly increase the pulse amplitude to the electrode until the amplitude nears the MTV of the previous electrode, then slowly increase until the patient indicates that the delivered stimulation is uncomfortable (step 355). Programmer will store the current amplitude as the maximum tolerance value (MTV) for that electrode (step 360). This electrode combination is now calibrated for PV values, and optionally for MTV values.

Preferably, in this embodiment, the amplitude increase between the PV and the MTV is done in a similar logarithmic fashion, so that the increase within the projected tolerable range (between the PV for that electrode and the MTV of the first electrode) is relatively fast, but slows considerably as the amplitude nears the MTV of the first electrode, so as to cause as little discomfort as possible to the patient during the calibration process.

The calibration process then repeats for the remaining electrode combinations or pairs, and any other leads, until all electrodes are calibrated, and their PVs, and optionally MTVs, are stored (returning to step 340).

Note that the electrodes do not need to be calibrated in any particular order. A preferred approach is to calibrate the electrodes that are located at the extremes or "corners" of the IPG leads. During the process of doing so, the treating professional can generally define a "map" of the physical coverage area of the patient's body that can be effectively treated by the spinal stimulation.

In another embodiment, the calibrated electrodes are then used to create stimsets for treatment of the patient. In this case, after the initial calibration steps are taken to determine the perception value (PV) voltage for each electrode, the individual performing the calculation using the external programmer (the "operator", who may or may not also be the patient), will use the external programmer as follows.

The operator will select a valid electrode-polarity combination that he deems may be effective, and typically will also set the pulse width and frequency. Alternatively, the external programmer may select an electrode-polarity combination automatically. The external programmer will increase the pulse amplitude from zero volts to a calculated comfort value (CV) voltage in 5 logarithmic-like steps to determine if the calculated CV is the actual CV for that electrode combination.

If the calculated CV is too low, then the operator, using the external programmer, will increase the voltage using a linear voltage increase until the actual CV is determined.

Similarly, if the calculated CV is too high, then the operator, using the external programmer, will decrease the voltage using a linear voltage decrease until the actual CV is determined.

Once the actual CV is determined, that value is stored. Thereupon, the operator will proceed to set the PV. In this case, the external programmer will begin at zero volts and proceed, in two logarithmic-like steps, to the calculated PV. If the actual PV is not the same as the calculated PV, the actual PV is determined using a process as for the CV, above.

Once actual PV and actual CV are found, a calculated maximum tolerance value (MTV) is then set by doubling the voltage difference between PV and CV and adding the difference to PV. The stimset is now complete.

In this embodiment, the following symbols are used:

| | |
|---|---|
| $A_{C\text{-}RANGE}$ | Amplitude calibration range for a lead electrode. |
| $A_{T\text{-}RANGE}$ | Amplitude testing range for a lead electrode. |
| $A_{MT}$ | Maximum Tolerable amplitude setting recorded on the selected lead. |
| $A_{PER}$ | Perception amplitude setting for a lead electrode. |
| $A_{C\text{-}SP}$ | Sub-Perception calibration value for a lead electrode. |
| $A_{T\text{-}SP}$ | Sub-Perception testing value for a lead electrode. |
| $A_{MAX}$ | Maximum amplitude level to stop auto-ramping. |
| $A_{COMF}$ | The targeted Comfort amplitude for the selected cathodes. |
| $A_{STEP}$ | Target amplitude for current step. |

FIG. 4 depicts an exemplary diagram of relative amplitude measurements for electrode calibration, using the symbols described above. Note that this figure is not to scale, and actual relationships between different measurements will be according to the calculations described herein.

During the calibration process, a typical pulse frequency is 40 Hz with a pulse width of 208 microseconds. The initial perception level is found by auto-ramping the amplitude in 0.20 mA steps to a 12 mA limit. Typically, during an initial increase from zero, this ramping takes 10-15 seconds. For subsequent amplitude increases, or when the IPG responds to a command to increment amplitude, the ramp time is typically 2.0-3.5 seconds.

The Max Tolerable amplitude is found by manually ramping the amplitude, preferably using a 0.20 mA step size to a 25.50 mA manual ramp limit.

After the first electrode's $A_{PER}$ and $A_{MT}$ are found, the amplitude range for each other cathode on the lead is calculated as $A_{C\text{-}RANGE} = (A_{MT} - A_{PER(1)})$. If $A_{C\text{-}RANGE} \leq 1.00$ mA, the calibration procedure is stopped and only manual stimset testing is performed.

The Sub-perception is calculated and rounded down to the nearest 0.20 mA for the starting amplitude level for the current cathode. This is calculated using $$A_{C\text{-}SP(n)} = A_{PER(n-1)} - \frac{A_{C\text{-}RANGE}}{4},$$

where n is the number of the current cathode.

Other perception levels are then found using the step size and ramp speed described above. The range of automatic amplitude ramping for other perception values are found by first calculating $A_{MAX}$ for the current cathode using $$A_{MAX(n)} = A_{C\text{-}SP(n)} + \frac{A_{C\text{-}RANGE}}{2},$$

where n is the number of the current cathode. The amplitude for the cathode is automatically increased from $A_{C\text{-}SP}$ to $A_{MAX}$ or until the perception setting is recorded. After the $A_{MAX}$ limit is reached, if the perception setting has not yet been recorded, manual amplitude increases are used.

After the calibration is complete, the recorded Perception and Maximum Tolerable settings are used in a calibrated testing process to quickly reach the targeted Comfort amplitude. First, the target Comfort amplitude is calculated, using the lowest $A_{PER}$ and $A_{MT}$ of the selected cathodes:

$$A_{COMF} = A_{PER} + \frac{(A_{MT} - A_{PER})}{2}.$$

Next, the target Sub-Perception amplitude is calculated using the lowest $A_{PER}$, and $A_{MT}$ of the selected cathodes: $A_{T\text{-}SP} = A_{PER} - ((A_{MT} - A_{PER})/4)$. If $A_{T\text{-}SP} < 0$, then $A_{T\text{-}SP} = 0$.

Next the range from Sub-Perception to the Comfort amplitude is calculated: $A_{T\text{-}RANGE} = A_{COMF} - A_{T\text{-}SP}$.

Next, the increment step to reach the target comfort level is calculated using the following table, rounding down to the nearest 0.10 mA:

| Target Amplitude | If $A_{T\text{-}SP} < 0$ | If $A_{T\text{-}SP} = 0$ |
|---|---|---|
| $A_{STEP(1)}$ | $A_{T\text{-}SP}$ | $0.45 * A_{T\text{-}RANGE}$ |
| $A_{STEP(2)}$ | $A_{T\text{-}SP} + 0.45 * A_{T\text{-}RANGE}$ | $0.70 * A_{T\text{-}RANGE}$ |
| $A_{STEP(3)}$ | $A_{T\text{-}SP} + 0.725 * A_{T\text{-}RANGE}$ | $0.85 * A_{T\text{-}RANGE}$ |
| $A_{STEP(4)}$ | $A_{T\text{-}SP} + 0.90 * A_{T\text{-}RANGE}$ | $0.90 * A_{T\text{-}RANGE}$ |
| $A_{STEP(5)}$ | $A_{COMF}$ | $A_{COMF}$ |

To reach the target perception amplitude from zero in two steps, the system uses the lowest APER of the selected electrode combination and calculates 75% for the first amplitude increase: $A_{STEP(1)} = 0.75 * A_{PER}$.

The second amplitude increase is: $A_{STEP(2)} = A_{PER}$.

The amplitude step size returns to the default value as the amplitude is manually adjusted to find the actual Comfort amplitude.

If an existing stimulation setting is to be used for calibrated testing, the existing parameters from the stimulation setting are used as follows:

$A_{PER}$ The existing Perception Value for the stimulation setting.

$A_{COMF}$ The difference between the existing Maximum Tolerable value and the existing Perception value for the stimulation setting:

$$A_{COMF} = A_{PER} + \frac{(A_{MT} - A_{PER})}{2}.$$

Any time during the calibrated testing, the current pulse width can be changed within defined limits. If the pulse width is changed, the amplitude must be compensated using $$A_{NEW} = \frac{PW}{PW_{NEW}} A$$

where:
PW Pulse width used during calibration
$PW_{NEW}$ New pulse width setting
A Current amplitude setting
$A_{NEW}$ New amplitude setting FIG. 5 depicts a flowchart of a process in accordance with a preferred embodiment, as described in detail above. First, the electrode polarities are set for a stimset to be tested (step 505).

From the previously-determined PV and MTV for each of the selected cathodes in the stimset, a projected comfort value is calculated and amplitude comfort value ramp steps are determined (step 510).

Next, the amplitude delivered to the lead electrodes is ramped up to the comfort value according to the comfort value ramp steps (step 515).

Next, the amplitude is reset to a predetermined, sub-perception value, preferably zero mA (step 520).

From the previously-determined PV for each of the selected electrodes in the stimset, a projected perception value is calculated and amplitude perception value ramp steps are determined (step 525).

Next, the amplitude delivered to the lead electrodes is ramped up to the perception value according to the comfort value ramp steps, until the patient indicates she perceives the stimulation (step 530).

Next, based on the comfort value and the perception value, the maximum tolerable value is calculated (step 535).

Finally, the stimulation settings, including electrode polarities, pulse frequency, and the values determined above, are stored (step 540).

Those skilled in the art will recognize that, for simplicity and clarity, the full structure and operation of all devices and processes suitable for use with the present invention are not being depicted or described herein. Instead, only so much of an implantable pulse generator and supporting hardware as is unique to the present invention or necessary for an understanding of the present invention is depicted and described. The remainder of the construction and operation of the IPGs described herein may conform to any of the various current implementations and practices known in the art.

Those of skill in the art will also recognize that not all steps in the above-described processes must be performed in the order described. Further, not all steps of any process, particularly the optional steps, must necessarily be performed in conjunction with all other steps, and can be omitted from the process or performed independent of other steps of the process.

It is important to note that while the present invention has been described in the context of a fully functional system, those skilled in the art will appreciate that at least portions of the mechanism of the present invention are capable of being distributed in the form of an instruction set contained within a machine usable medium in any of a variety of forms, and that the present invention applies equally regardless of the particular type of instruction or signal bearing medium utilized to actually carry out the distribution. Examples of machine usable mediums include: nonvolatile, hard-coded type mediums such as read only memories (ROMs) or erasable, electrically programmable read only memories (EEPROMs), user-recordable type mediums such as floppy disks, hard disk drives and compact disk read only memories (CD-ROMs) or digital versatile disks (DVDs), and transmission type mediums such as digital and analog communication links.

Although an exemplary embodiment of the present invention has been described in detail, those skilled in the art will understand that various changes, substitutions, variations, and improvements of the invention disclosed herein may be made without departing from the spirit and scope of the invention in its broadest form.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 U.S.C. § 112 unless the exact words "means for" are followed by a participle.

It may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and if the term "controller" is utilized herein, it means any device, system or part thereof that controls at least one operation, whether such a device is implemented in hardware, firmware, software or some combination of at least two of the same. It should be noted that the functionality associated with any particular controller may be centralized or distributed, whether locally or remotely.

What is claimed is:

1. A method for calibrating electrodes of a stimulation device, comprising:
   placing a stimulation device in a programming mode using an external programming device, the external programming device adapted to control the stimulation device, the stimulation device having a plurality of electrodes positioned to stimulate nerves of a patient;
   activating a first electrode combination using a pulse stimulation with an amplitude such that the stimulation is not perceived by the patient;
   increasing the amplitude of the pulse stimulation according to a first function until the pulse stimulation is perceived by the patient;
   storing a measure of the amplitude as a perception value for the first electrode combination;
   activating a second electrode combination using a pulse stimulation with an amplitude such that the stimulation is not perceived by the patient;
   increasing the amplitude of the pulse stimulation according to a second function until the pulse stimulation is perceived by the patient, said second function based on said stored perception value, wherein the amplitude is increased for the second electrode combination until the amplitude nears the stored perception value for the first electrode combination; and
   storing a measure of the amplitude as a perception value for the second electrode combination.

2. The method of claim 1 further comprising increasing the amplitude of the pulse stimulation linearly until the patient indicates that the pulse stimulation has approached a maximum tolerable amount, and storing a measure of the amplitude as a maximum tolerance value for the first electrode combination.

3. The method of claim 1 wherein amplitude increases are performed automatically by the external programming device.

4. The method of claim 1, wherein at least one of the amplitude increases is performed by an operator's manual control of the external programming device.

5. The method of claim 1, wherein said second electrode combination is activated with a zero amplitude stimulation current.

6. The method of claim 5, wherein said second function increases the amplitude of a pulse stimulation from zero amplitude to an amplitude value based on said stored perception value.

7. The method of claim 1 wherein said external programming device stores at least one program for activating the stimulation device electrodes.

8. The method of claim 1 wherein said stimulation device stores at least one program for activating the stimulation device electrodes.

9. The method of claim 1 wherein at least one of said activating, increasing, and storing are performed on an additional electrode combination.

10. The method of claim 1 further comprising:
deactivating said first electrode combination before selecting said second electrode combination.

11. A method for calibrating electrodes of a stimulation device, comprising:
placing a stimulation device in a programming mode using an external programming device, the external programming device adapted to control the stimulation device, the stimulation device having a lead with a plurality of electrodes, the electrodes positioned to stimulate nerves of a patient;
determining a perception value for the pulse amplitude of a first electrode combination;
determining a maximum tolerance value for the pulse amplitude of the first electrode combination;
calculating a calibration range value, a sub-perception value, and a maximum level value according to the perception value and maximum tolerance value of the pulse amplitude of the first electrode combination;
calculating a target comfort value for a plurality of electrode combinations; and
determining a respective comfort value for each electrode combination of the plurality of electrode combinations by non-linearly ramping amplitudes of pulses applied to the patient to a respective target comfort value such that amplitude steps between pulses decrease as the amplitude of pulses near the respective target comfort value.

12. The method of claim 11, further comprising determining a perception value for a second electrode combination by increasing the amplitude of the pulse stimulation linearly from the sub-perception value until the pulse stimulation is perceived by the patient.

13. The method of claim 11, wherein the target comfort value for each electrode combination is the average of the maximum tolerance value and the perception value for that electrode combination.

14. The method of claim 11, further comprising calculating a testing range value and calculating amplitude step sizes as a function of the testing range value and the sub-perception value.

15. The method of claim 1 wherein the sub-perception pulse amplitude value is zero.

16. A programming device for programming an implantable pulse generator, the programming device comprising:
communication circuitry for communicating with the implantable pulse generator; and
a processor for controlling the programming device, the processor operating under the control of executable instructions, the executable instructions comprising:
code for communicating one or more commands to the implantable pulse generator to generate one or more electrical pulses at a defined amplitude for application to a patient;
code for calculating a respective target comfort level for each electrode combination of a plurality of electrode combinations using at least a previously determined perception amplitude value; and
code for applying a plurality of pulses to the patient for each electrode combination of the plurality of electrode combinations to determine a respective comfort level for each electrode combination by non-linearly ramping amplitudes of pulses applied to the patient to a respective target comfort value such that amplitude steps between pulses decrease as the amplitude of pulses near the respective target comfort value.

17. The programming device of claim 16 wherein the executable instructions further comprise:
code for calculating a plurality of amplitude steps for use by the code for applying, wherein the code for calculating the plurality of amplitude steps uses a function that depends on the previously determined perception amplitude and a previously determined maximum amplitude values.

18. The programming device of claim 17 wherein a single maximum comfort value is used for each electrode combination.

19. The programming device of claim 16 wherein a respective perception amplitude value is determined for each electrode combination for use by the code for applying.

20. The programming device of claim 19 wherein the perception amplitude values for the plurality of electrode combinations are determined in succession by ramping to an amplitude in a non-linear manner such that the amplitude steps decrease in size as the ramped amplitude approaches a previously determined perception amplitude value.

21. The programming device of claim 16 wherein the executable instructions further comprise:
code for processing input from an operator of the programming device to manually adjust an amplitude of applied pulses after the code for applying automatically applies multiple amplitude-ramped pulses.

\* \* \* \* \*

UNITED STATES PATENT AND TRADEMARK OFFICE
CERTIFICATE OF CORRECTION

PATENT NO. : 7,254,446 B1 Page 1 of 1
APPLICATION NO. : 11/073026
DATED : August 7, 2007
INVENTOR(S) : John H. Erickson, Thomas K. Hickman and Erik D. Engstrom It is certified that error appears in the above-identified patent and that said Letters Patent is hereby corrected as shown below:

Claim 15, "claim 1" should read --claim 11--.

Signed and Sealed this

Thirtieth Day of October, 2007

JON W. DUDAS
*Director of the United States Patent and Trademark Office*